(12) United States Patent
Gandhi (10) Patent No.: US 9,579,425 B2
(45) Date of Patent: Feb. 28, 2017

(54) CATION EXCHANGE URETERAL STENT

(71) Applicant: Cook Medical Technologies LLC, Bloomington, IN (US)

(72) Inventor: Neena Gandhi, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 53 days.

(21) Appl. No.: 14/136,969

(22) Filed: Dec. 20, 2013

(65) Prior Publication Data

US 2014/0188248 A1 Jul. 3, 2014

Related U.S. Application Data

(60) Provisional application No. 61/746,887, filed on Dec. 28, 2012.

(51) Int. Cl.

| | | |
|---|---|---|
| *A61F 2/04* | (2013.01) | |
| *A61L 31/04* | (2006.01) | |
| *A61L 31/14* | (2006.01) | |
| *A61L 31/16* | (2006.01) | |
| *A61M 27/00* | (2006.01) | |
| *B01J 39/04* | (2006.01) | |

(Continued)

(52) U.S. Cl.
CPC .............. *A61L 31/042* (2013.01); *A61F 2/04* (2013.01); *A61L 31/145* (2013.01); *A61L 31/16* (2013.01); *A61M 27/008* (2013.01); *B01J 39/043* (2013.01); *B01J 39/10* (2013.01); *B01J 39/12* (2013.01); *B01J 39/14* (2013.01); *B01J 39/20* (2013.01); *B01J 41/125* (2013.01); *B01J 45/00* (2013.01); *A61F 2002/048* (2013.01); *A61L 2420/04* (2013.01)

(58) Field of Classification Search
CPC .......... A61F 2002/047; A61F 2002/048; A61F 2/0018
See application file for complete search history.

(56) References Cited

U.S. PATENT DOCUMENTS

| | | | |
|---|---|---|---|
| 3,184,381 | A | 5/1965 | Harvey et al. |
| 4,790,809 | A | 12/1988 | Kuntz |

(Continued)

FOREIGN PATENT DOCUMENTS

| | | |
|---|---|---|
| EP | 0065884 | 12/1982 |
| EP | 2537415 | 12/2012 |
| GB | 1132233 | 10/1968 |

OTHER PUBLICATIONS

Aqualon, Klucel (hydroxypropylcellulose) Physical and Chemical Properties, 2001, Hercules Incorporated, pp. 2-23.*

(Continued)

*Primary Examiner* — Thomas J Sweet
*Assistant Examiner* — Wade P Schutte
(74) *Attorney, Agent, or Firm* — Brinks Gilson & Lione (57) ABSTRACT

An endoluminal prosthesis for placing in a body passage of a patient, includes a ureteral stent, the ureteral stent having a generally tubular housing having a proximal end and a distal end and a lumen longitudinally disposed therethrough, with cation-exchange resin beads disposed within the tubular housing, and at least one anchoring mechanism disposed on a distal end of the tubular housing, where at least one retention screen is disposed within the lumen of the ureteral stent configured to retain the plurality of beads.

20 Claims, 5 Drawing Sheets

(51) Int. Cl.
| | |
|---|---|
| *B01J 39/10* | (2006.01) |
| *B01J 39/12* | (2006.01) |
| *B01J 39/14* | (2006.01) |
| *B01J 39/20* | (2006.01) |
| *B01J 41/12* | (2006.01) |
| *B01J 45/00* | (2006.01) |

(56) References Cited

U.S. PATENT DOCUMENTS

| | | |
|---|---|---|
| 2005/0125020 A1* | 6/2005 | Meade et al. ............... 606/191 |
| 2005/0153379 A1 | 7/2005 | Hoon et al. |
| 2007/0207186 A1 | 9/2007 | Scanlon et al. |
| 2008/0051696 A1* | 2/2008 | Curtin ............... A61M 1/1696 604/29 |
| 2008/0183278 A1 | 7/2008 | Atanasoska et al. |
| 2008/0200976 A1 | 8/2008 | Asgari |
| 2009/0011445 A1 | 1/2009 | Hoon et al. |
| 2009/0187254 A1 | 7/2009 | Deal et al. |
| 2009/0317488 A1 | 12/2009 | Mehta et al. |
| 2010/0145467 A1 | 6/2010 | Davoudi et al. |
| 2010/0256729 A1* | 10/2010 | Mangiardi ............... 623/1.15 |
| 2010/0298948 A1* | 11/2010 | Hoey et al. ............... 623/23.7 |
| 2012/0015030 A1 | 1/2012 | Mehta et al. |
| 2012/0035499 A1 | 2/2012 | Hoon et al. |

OTHER PUBLICATIONS

Extended European Search Report, EU Patent Application No. 13198358.7, report dated Apr. 1, 2014, 7pp.

Rugendorff et al., "Cation exchange resin preparation in recurrent calcium urolithiasis", Urology, vol. 22, Issue 2, Aug. 1983, pp. 143-150.

* cited by examiner

CATION EXCHANGE URETERAL STENT

RELATED APPLICATIONS

The present application claims priority to U.S. Provisional Patent Application Ser. No. 61/746,887 filed Dec. 28, 2012, the entirety of which is hereby incorporated by reference.

TECHNICAL FIELD

The invention relates generally to medical devices and, particularly, medical devices useful for urinary drainage.

BACKGROUND

Minimally-invasive surgery has evolved to a point where procedures that were unimaginable a few years ago are now routinely performed on a daily basis. Indwelling ureteral stents have been widely used for years. Such stents are placed in the ureter, which is the duct between the kidney and the bladder, for the purpose of establishing and/or maintaining an open, patent flow of urine from the kidney to the bladder.

Nephrolithiasis is a condition in which one or more calculi or stones are present in the kidneys. Kidney stones affect 3-5% of the world population and 80% of the stones are calcium-based; calcium oxalate being predominant. Other stones are made up of calcium phosphate, uric acid, cystine or struvite (magnesium ammonium phosphate). Small crystal aggregates are typically excreted from the body via passage in urine. Once the aggregrates grow to a certain size (3 mm) however, they can cause obstruction of the ureters due to urolithiasis.

Ureteral stents may be used to retain patency of the ureteral lumen and to continue normal urinary drainage following the treatment and removal of stones and calculi from kidneys and ureters. To treat this condition, several individual steps are involved. In one procedure, these steps include placing a relatively narrow wire guide through a urethra and bladder, and then through the ureter and into the kidney. After the wire guide is placed, a catheter is run along the wire guide, dilating the body passage (the urethra and the ureter) as it moves down the wire guide. The access sheath also dilates the body passages as it moves from outside the body, through the urethra, and into the ureter, down the desired location, and into or very near the kidney.

The physician may then remove calculi and stones through the access sheath, using a grasper, a retrieval basket or other device. The access sheath protects the ureter from repeated passage of the retrieval device while the stones or calculi are removed. After the stones are removed, the ureteral stent may be placed into the ureter through the access sheath, using the catheter or a pushing tube to position the stent.

Lifetime risk of nephrolithiasis in the developed world is 10-15%, and is higher elsewhere (20-25% in the Middle East). In the US, nephrolithiasis is estimated to occur in up to 10% and 5% of the male and female population respectively, result in medical costs of $2.1 billion annually. 70% of those who experience nephrolithiasis will have recurrence of stones even after surgical removal. Once recurrent, the subsequent risk of relapse is raised and the interval between recurrences is shortened. Crystallization of calcium and magnesium salts is the chief culprit in the formation of kidney stones.

The typical ureteral stent can be composed of various radiopaque polymers, including polyethylene, silicone, polyurethane, and thermoplastic elastomer. These stents are retained in the ureter by a retentive anchoring portion, such as a curved shape, pigtail, coil, J-shape, or hook configuration, at either end of the stent that engages the walls of the bladder and the kidney, respectively. The stent is resilient to allow it to be straightened for insertion into a body passageway and returned to its predetermined retentive anchoring shape when in situ. There can be problems, however, with ureteral stents, as urine may fail to drain through the stent. This may be due to a number of reasons, such as extrinsic compression of the stent or blockage of the drainage mechanism of the stent by encrustation. Furthermore, there can be problems associated with migration of the ureteral stent from the original implantation site either upward into the kidney of the patient or downward into the bladder of the patient.

BRIEF SUMMARY

In one aspect, an endoluminal prosthesis for placing in a body passage of a patient, includes a ureteral stent, the ureteral stent comprising a generally tubular housing having a proximal end and a distal end and a lumen longitudinally disposed therethrough, a plurality of beads disposed within the lumen of the tubular housing, the beads comprising ion exchange resin material, at least one anchoring mechanism disposed on a distal end of the tubular housing, where at least one retention screen is disposed within the lumen of the ureteral stent configured to retain the plurality of beads. In some embodiments, the ion exchange material comprises a sulfopropyl or sulfonate group bonded to a biocompatible polymeric material. In other embodiments, the beads are microporous or nanoporous.

In yet another aspect, a kit for introducing an endoluminal prosthesis includes a ureteral stent, the ureteral stent comprising a generally tubular housing having a proximal end and a distal end and a lumen longitudinally disposed therethrough, a plurality of beads disposed within the lumen of the tubular housing, the beads comprising ion exchange resin material, and at least one anchoring mechanism disposed on a distal end of the tubular housing; an introduction assembly, the introduction assembly comprising a wire shaft having a proximal end and a distal end and a first magnet connected to the distal end of the wire shaft; and an access sheath surrounding the ureteral stent and the introduction assembly, where the first magnet is configured to engage with a corresponding magnet on at least one anchoring mechanism and where at least one retention screen is disposed within the lumen of the ureteral stent configured to retain the plurality of beads. In some embodiments, the housing of the introducer assembly further includes a spring-loaded piston disposed within an interior surface.

In still another aspect, a method for implanting an endoluminal prosthesis into a body includes providing a ureteral stent, the ureteral stent having a generally tubular housing having a proximal end and a distal end and a lumen longitudinally disposed therethrough, a plurality of beads disposed within the lumen of the tubular housing, the beads comprising ion exchange resin material, and at least one anchoring mechanism disposed on a distal end of the tubular housing; engaging the ureteral stent with an introduction assembly, the introduction assembly comprising a wire shaft having a proximal end and a distal end and a first magnet connected to the distal end of the wire shaft; placing a wire guide along a body path to a location desired for the prosthesis, inserting an access sheath along the wire guide and advancing the access sheath to the desired position;

removing the wire guide; advancing the ureteral stent within the access sheath to the desired location using a stent positioner; and at least partially removing the access sheath and deploying the ureteral stent by disengaging the ureteral stent from the introduction assembly, where at least one retention screen is disposed within the lumen of the ureteral stent configured to retain the plurality of beads.

DETAILED DESCRIPTION OF THE DRAWINGS AND THE PRESENTLY PREFERRED EMBODIMENTS

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of and "consisting essentially of," the embodiments or elements presented herein, whether explicitly set forth or not.

The terms "about" or "substantially" used with reference to a quantity includes variations in the recited quantity that are equivalent to the quantity recited, such as an amount that is insubstantially different from a recited quantity for an intended purpose or function.

The term "prosthesis" means any device for insertion or implantation into, or replacement, for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway or tract may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include, without limitation, blood vessels, respiratory ducts, gastrointestinal ducts, such as the biliary duct, intestines, the esophagus, the pericardial cavity, the thoracic cavity, nephrostomy tracts, and the like. Accordingly, the terms "endoluminal device" or "endoluminal prosthesis" describe devices that can be placed inside or moved through any such lumen or duct.

The terms "patient," "subject," and "recipient" as used in this application may refer to any animal, particularly humans.

The terms "proximal" and "distal" will be used to describe opposing axial ends of the ureteral stent, as well as the axial ends of various component features. The term "proximal" is used to refer to the end of the ureteral stent (or component thereof) that is closest to the operator during use of the system. The term "distal" is used to refer to the end of the ureteral stent (or component thereof) that is initially inserted into the patient, or that is closest to the patient during use.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "medical device" means any object that is itself or that includes a component that is intentionally inserted into the body of a patient as part of a medical treatment, and that comprises a structure adapted for introduction into a patient. The medical device can be a tool, such as, without limitation, a catheter, a wire guide, a forceps, or a scissors used to affect a surgical procedure at and/or deliver a second medical device to a treatment site in a patient. An alternative medical device of the present invention is one that is commonly intended to be a permanent implant, such as a stent.

The term "implantable" refers to the ability of a medical device to be positioned, partially or wholly, at a location within a body of a human or veterinary patient for any suitable period of time, such as within a vessel. Implantable medical devices can include devices configured for bioabsorption within a body during prolonged period of time.

The term "controlled release" refers to the release of a material, such as a pharmacologically active ingredient, at a predetermined rate. A controlled release may be characterized by a drug elution profile, which shows the measured rate that the material is removed from a material-containing device in a given solvent environment as a function of time. A controlled release does not preclude an initial burst release associated with the deployment of the medical device. The release may be a gradient release in which the concentration of the material released varies over time or a steady state release in which the material is released in equal amounts over a certain period of time (with or without an initial burst release).

The term "pharmacologically active ingredient" refers to any agent that produces an intended therapeutic effect on the body to treat or prevent conditions or diseases.

A more detailed description of the embodiments will now be given with reference to FIGS. 1a-6. The present invention is not limited to those embodiments illustrated; it specifically contemplates other embodiments not illustrated but intended to be included in the claims.

Figure 1A:
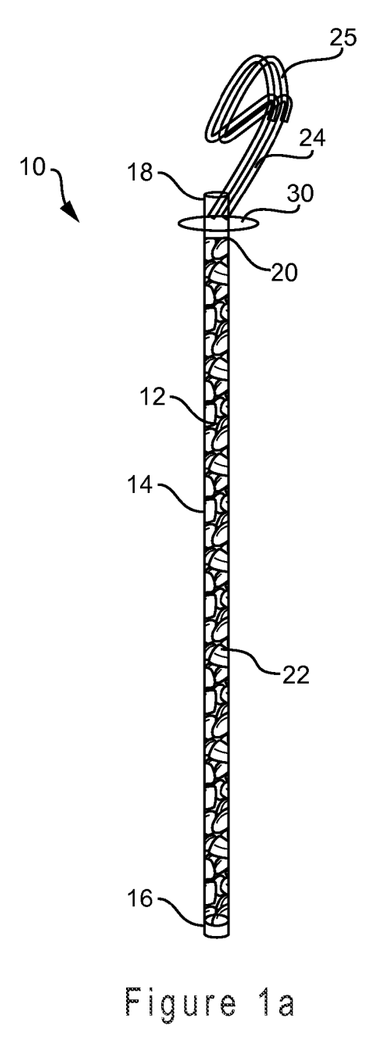
FIGS. 1a and 1b depicts an embodiment of an endoluminal prosthesis having ion exchange resin beads.
Figure 1B:
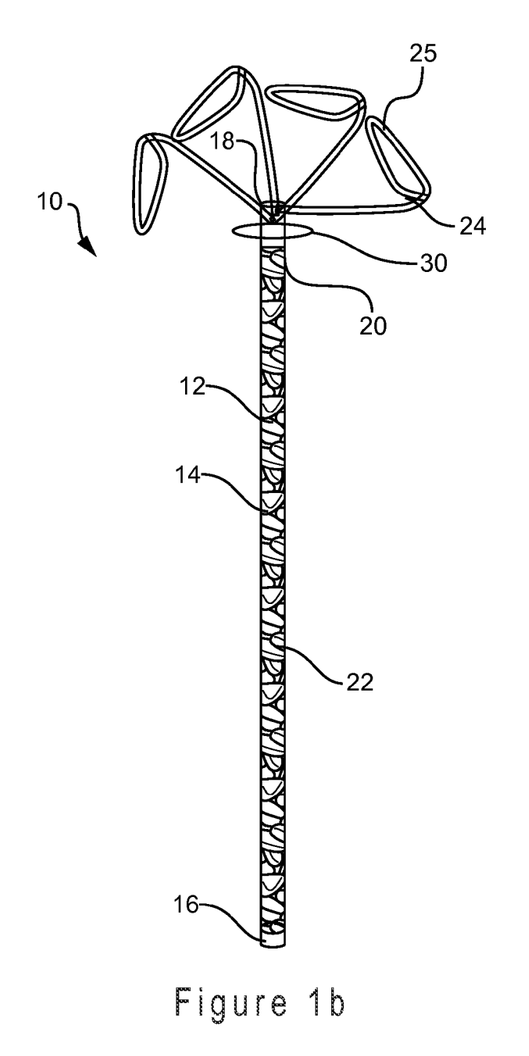

FIGS. 1a and 1b show an embodiment of an endoluminal prosthesis. As shown, the prosthesis 10 comprises a ureteral stent 12 having an elongated housing 14. The elongated housing 14 of the ureteral stent 12 has a generally tubular configuration. The ureteral stent 12 further includes a proximal end 16 and a distal end 18 and a lumen 20 disposed therethrough. A plurality of resin beads 22 are disposed within the lumen 20 of the ureteral stent 12 configured for cation exchange and/or adsorption. The ureteral stent 12 may have a length of about 12 cm to about 32 cm and preferably having outer diameters in the range of about 4 Fr to about 10 Fr. Disposed on the distal end 18 of the ureteral stent 12 is a tetracoil anchoring mechanism 24. The tetracoil anchoring mechanism 24 is configured to be positioned at the distal end of the ureter, preferably in close proximity to the ureteropelvic junction and within the kidney. In one embodiment, each of the coil wires 25 of the tetracoil anchoring mechanism 24 reaches out into different calyces and/or different parts of the renal pelvis. The position of the tetracoil anchoring mechanism 24 within the kidney prevents the ureteral stent 12 from falling out or migrating downward into the ureter. In other embodiments of the ureteral stent 12, the anchoring mechanism may comprise different configurations, including, but not limited to, a malecot or a pigtail configuration. In one embodiment, no portion of the ureteral stent 12 will be positioned in the trigonal area of the bladder when deployed within the ureter. The proximal end 16 of the ureteral stent 12 will be positioned in close proximity to, but distal of, the ureterovesical junction. In other embodiments, the proximal end of the stent may also include an anchoring mechanism such as those discussed above or others known to those skilled in the art, if so desired for the functioning of the device.

The tetracoil anchoring mechanism 24 has an open configuration and a collapsed configuration. In the collapsed configuration, as shown in FIG. 1a, the four coil wires 25 are in close contact with each other. The tetracoil anchoring mechanism 24 may be placed in the collapsed configuration through the use of an access sheath or other delivery device. In alternative embodiments, the tetracoil anchoring mechanism 24 may be further maintained in the collapsed configuration through the use of tether or a magnet. The width of the tetracoil anchoring mechanism 24 does not exceed the diameter of the stent by more than 3 Fr. In the open configuration, as shown in FIG. 1b, the four coil wires 25 of the tetracoil anchoring mechanism 24 expand radially apart from each other. In the open configuration, the expanded coil wires 25 together have a combined width of between about 8 Fr. to about 10 Fr.

Figure 2A:
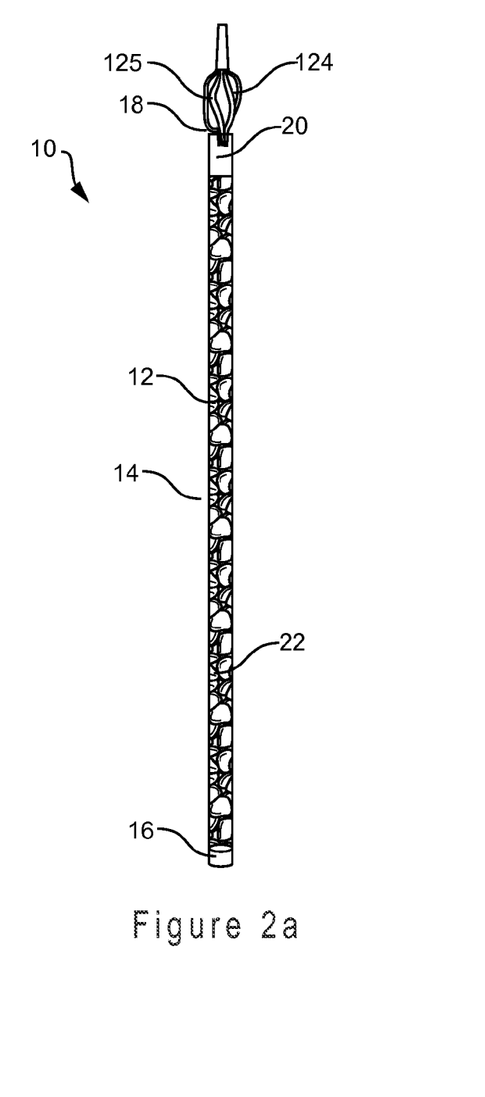
FIGS. 2a-2c depict alternative embodiments of retention members for use with the ureteral stent of FIG. 1.
Figure 2B:
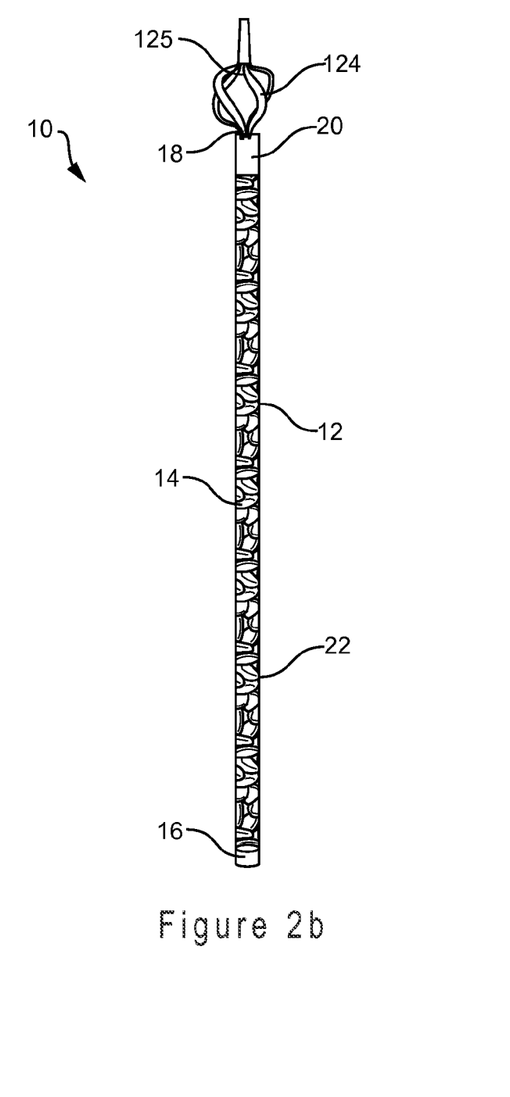
Figure 2C:
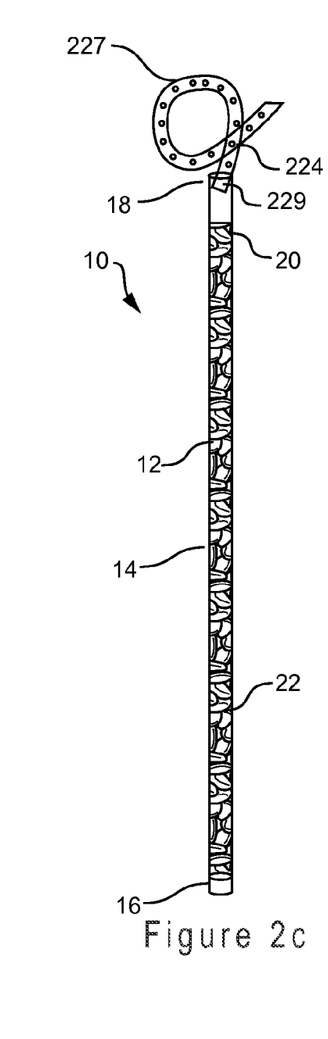

FIGS. 2a-2c show alternative embodiments of an anchoring mechanism on the ureteral stent 12. FIGS. 2a and 2b shows a distal anchoring mechanism 124 having a generally malecot configuration having an outlet. The distal anchoring mechanism 124 in this embodiment has a collapsed configuration and an open configuration. When the anchoring mechanism 124 is in the collapsed configuration, as shown in FIG. 2a, the wires 125 of the anchoring mechanism 124 are disposed in close proximity with a longitudinal axis of the elongate housing 14. When the anchoring mechanism 124 is in the open configuration, as shown in FIG. 2b, the wires 125 of the anchoring mechanism 124 expand radially about the distal end 18 of the ureteral stent 12. FIG. 2c shows an anchoring mechanism 224 having a generally pigtail shape having a plurality of openings 227. The anchoring mechanism 224 includes an outlet 229 on its proximal end that is in fluid communication with the lumen 20 of the ureteral stent 12.

Referring back to FIGS. 1a and 1b, the ureteral stent 12 further includes a radiopaque flange 30 disposed on an outer surface of the ureteral stent 12. As shown, the radiopaque flange 30 is positioned proximal to the tetracoil anchoring mechanism 24 on the distal end 18 of the ureteral stent 12. In this embodiment, the radiopaque flange 30 has a generally circular configuration. In other embodiments, the radiopaque flange may have a different configuration, including, but not limited to, hemispherical, triangular elliptical, and rectangular. The radiopaque flange 30 helps the physician position the ureteral stent 12 within the ureter. Further, the radiopaque flange 30 has a diameter that is about 2 Fr to about 3 Fr greater than the diameter of the ureteral stent in order to prevent upward migration of the ureteral stent 12 when it is fully deployed within the ureter. The radiopaque flange 30 may be manufactured from any suitable biocompatible material, include, but not limited to, polyester-based biocompatible polymers, nylon-based polymers, polytetrafluoroethylene (PTFE) polymers, silicone polymers, polyurethane polymers, polyethylene polymers, and thermoplastic polymers.

Figure 3:
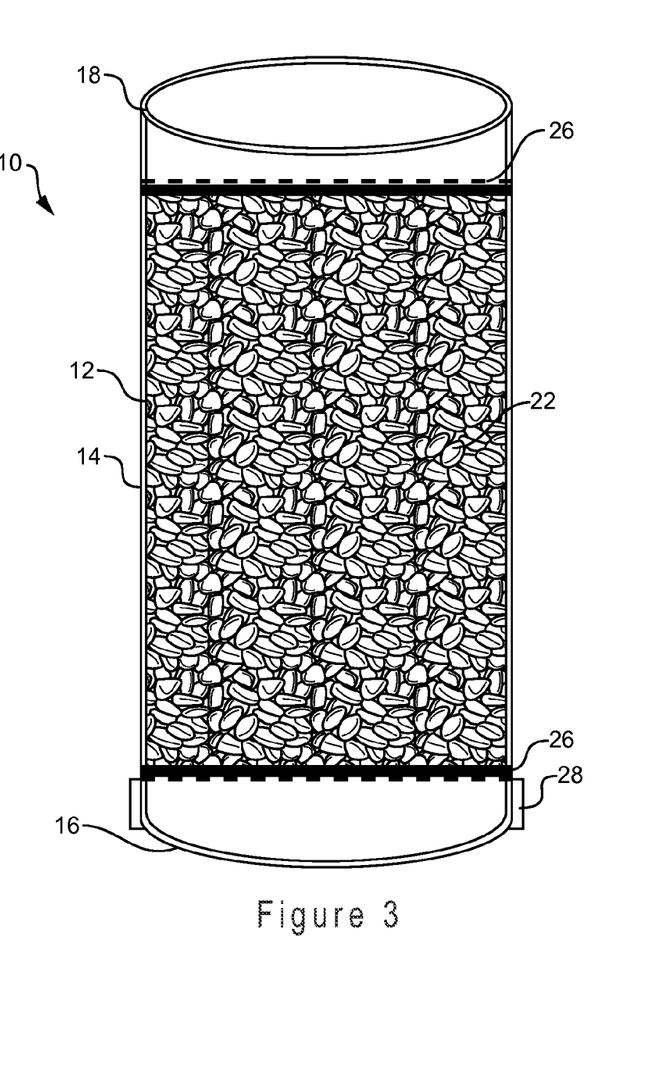
FIG. 3 depicts a portion of the elongate housing of the ureteral stent of FIG. 1.

FIG. 3 shows a portion of an embodiment of the ureteral stent 12 in greater detail. As shown, the resin beads 22 are in a packed bed configuration, where the resin beads 22 serve as the stationary phase. A pair of retention screens 26 are disposed on the proximal end 16 and the distal end 18 of the ureteral stent 12. The retention screens 26 are configured to contain the resin beads 22 within the elongated housing 14, while allowing urine to flow through the lumen 20 of the ureteral stent 12. In particular, the retention screens 26 are porous with a diameter sized to be less than the diameter of the resin beads 22. In this embodiment, a magnet 28 is disposed on the outer surface of the proximal end 16 of ureteral stent 12. As will be discussed below, the magnet 28 may interact with a corresponding magnet on an introduction assembly used in a delivery system for the ureteral stent 12 to help keep the tetracoil anchoring mechanism 24 in a collapsed configuration.

The resin beads 22 may have a diameter equal to or less than 200 nm, which helps form a stationary phase having a high surface area. The density of the packaged resin beads 22 (i.e. how tightly the resin beads 22 are packed within the ureteral stent 12) may be modified depending on the amount of clearance needed in order to allow for the flow of urine through the ureteral stent 12. Preferably, the resin beads 22 are loosely packed within the lumen 20 of the ureteral stent 12, which helps prevent any obstruction of urine flow. The resin beads 22 may be non-porous or porous. The porosity of the individual resin beads 22 may be modified in order to promote a desired amount of urine flow throughout the ureteral stent 12. In embodiments where the resin beads are porous, the pores are preferably microporous or nanoporous. The microporous or nanoporous beads provide a greater surface area and may permit a longer residence time within the ureteral stent 12 for an ion exchange to take place. In situations where a slower urine flow rate is desired (i.e. 1 mL/min), embodiments comprising non-porous beads may provide sufficient urine flow balance. Furthermore, the ureteral stent 12 may comprise a combination of porous and non-porous beads.

The resin beads 22 are typically made from biocompatible materials. Materials suitable for the resins beads 22 are those that remain both mechanically and chemically stable in the pH range 6-8. A strong cation exchanger group such as sulfopropyl or sulfonate may be bonded to a biocompatible polymeric material. Examples of suitable biocompatible materials include Chitosan-Carboxymethylcellulose, Zeolites, Phenolsulfonates, Acrylate-divinyl benzene, Sulfonated polystyrene-divinylbenzene, Carboxylic acid resins, Nanoporous silica, Cellulose and phosphate or carbonic cellulose derivatives, Collagen and phosphate or carbonic collagen derivatives, Methacrylate polymers, Agarose-polyacrolein, Alginate, Polyvinyl alcohol sponge, EDTA and other metal chelators. The ureteral stent 12 may comprise resin beads 22 manufactured from the same ion exchange material, or it may comprise resin beads 22 manufactured from a combination of suitable ion exchange materials.

In use, urine will pass through the lumen 20 of the ureteral stent 12. The urine includes divalent salts, having calcium and magnesium cations, which are insoluble in urine and are believed to contribute to urolithiasis within the patient. As the urine passes through the resin beads 22, the cations of the divalent salts within the urine will come into contact with the resin beads 22. Once in contact with the resin beads 22, the calcium and magnesium cations are adsorbed onto the resin beads 22, while hydrogen ions from the resins replace the cations in urine. This ion exchange is due to the greater affinity of the resin beads 22 to the divalent cations as compared to the monovalent hydrogen or other cations within the resin beads 22. The exchanged hydrogen cations form acids or monovalent salts within the urine. These monovalent salts are soluble and will dissolve in the urine that exits the ureteral stent. As such, buildup of insoluble salt crystals that could potentially obstruct the urinary tract is prevented.

In some embodiments, the ureteral stent 12 further includes a hydrogel film having ion exchange properties disposed on an outer surface of the elongated body 14. The film comprises ion exchange material intermixed with a base polymer. In order to create the elongated body 14 having the ion exchange material, a film may be produced by dispersion of colloidal or finely ground ion exchange materials into the base polymer, followed by rolling, compressing or extrusion. This film is then coated onto the elongated housing 14 of the ureteral stent 12. The proportion of ion exchange materials to base polymer may vary from 1:1 to 3:1 by volume. In some embodiments, the ion exchange materials used in the hydrogel film and the resin beads are the same. Alternative embodiments may use different ion exchange materials for the hydrogel resin beads and the hydrogel film.

One or more pharmacologically active agents, such as medications or drugs, may be placed on the outer surface of the elongate body 14 of the ureteral stent 12 or on the resin beads 22 in order to assist in patient care and comfort. For instance, an antimicrobial drug may help to reduce inflammation and microbial activity in the vicinity of the stent. Analgesics, such as aspirin or other non-steroidal anti-inflammatory drugs, may also be applied to the surface to reduce pain and swelling upon implantation of the stent. Other medications, such as alpha-blockers, may also be used. Alpha-blockers are drugs that block receptors in arteries and smooth muscles. In the urinary tract, alpha-blockers relax the walls of the tract and enhance urinary flow. Examples of suitable alpha-blockers include, but are not limited to, doxazosin, alfuzosin, tamsulosin, prazosin, and terazosin. Any of these pharmacologically active agents is preferably applied in a controlled release so that the beneficial effect of the drug is sustained over a period of at least several weeks or months. This may be especially helpful in cases where the stent will remain in place for a considerable length of time.

Embodiments of the ureteral stent 12 comprising pharmacologically active elements may be used for prophylactic applications as well as therapeutic applications. The drug of interest may be covalently bound to the surface of the resin beads 22 or housing 14 so that the drug remains active at the surface. In other embodiments, the drug may be bound to the resin beads 22 or housing 14 through other suitable means including electrostatic or adsorptive forces, which allows the drug to elute over the course of the indwelling period of the prosthesis, permitting a gradual and continual release of high local drug concentrations. Suitable particular applications for a drug eluting prosthesis may include modulation of urine components or pH, taking advantage of the specific and non-specific binding of various chemicals to different polymers.

In alternative embodiments, the polymers used for manufacture of the resin beads 22, anchoring mechanism 24, and the elongated body 14 of the ureteral stent 12 may be bio-resorbable. Bio-resorbable polymers are typically water-soluble polymers such as polylactic acid and polyglycolic acid, which will typically be absorbed within the body after a certain length of time due to dissolution, disintegration, fragmentation etc. as a response to physiological agents such as temperature, pH, ionic strength, etc. or merely with time. The use of bio-resorbable polymers can help in drug delivery as well as eliminate the necessity of having to remove the prosthesis following the required indwell.

Figure 4:
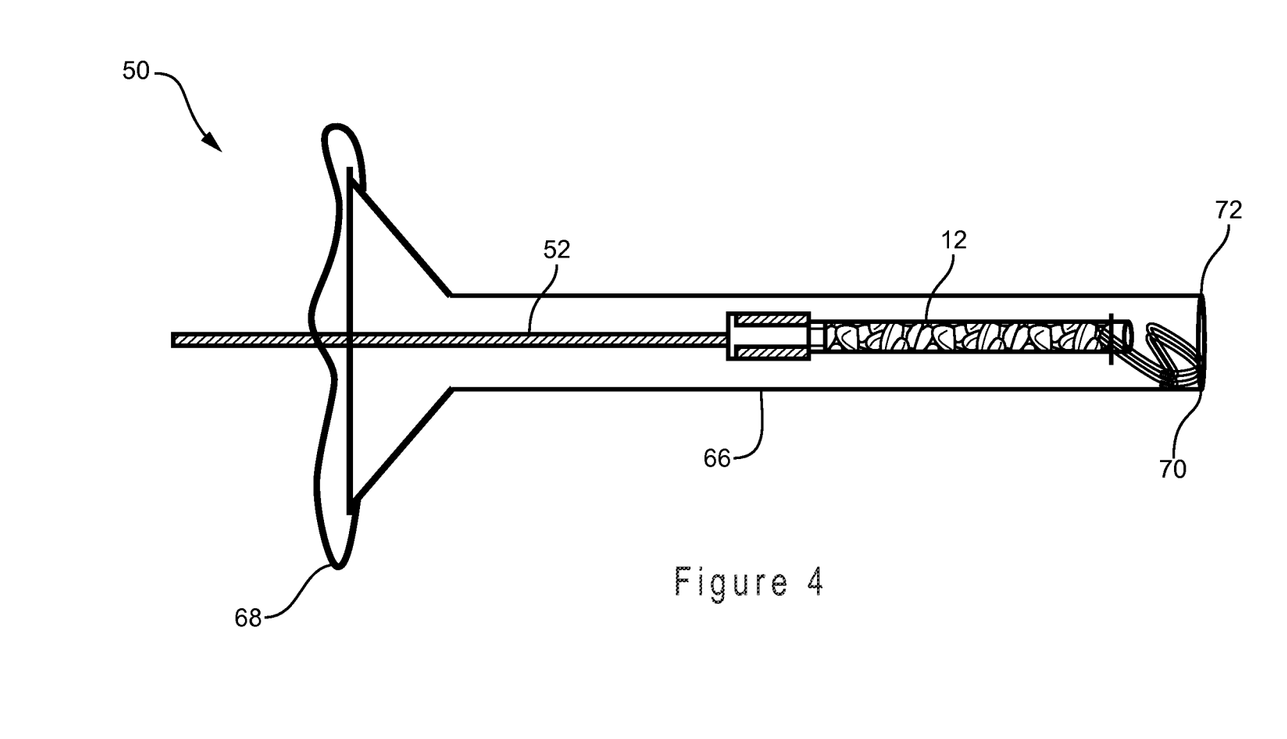
FIG. 4 depicts a kit for delivering the ureteral stent of FIG. 1.

FIG. 4 depicts an embodiment of a kit 50 for delivering the ureteral stent 12. As shown in FIG. 4a, the kit 50 comprises an introduction assembly 52, a ureteral access sheath 66, and the ureteral stent 12. The access sheath 66 includes a proximal end 68 and a distal end 70. An opening 72 is provided on the distal end 70 of the access sheath 66. The access sheath 66 may be made from any suitable biocompatible material, for example polytetrafluoroethylene (PTFE), nylon, or polyethylene.

Figure 5A:
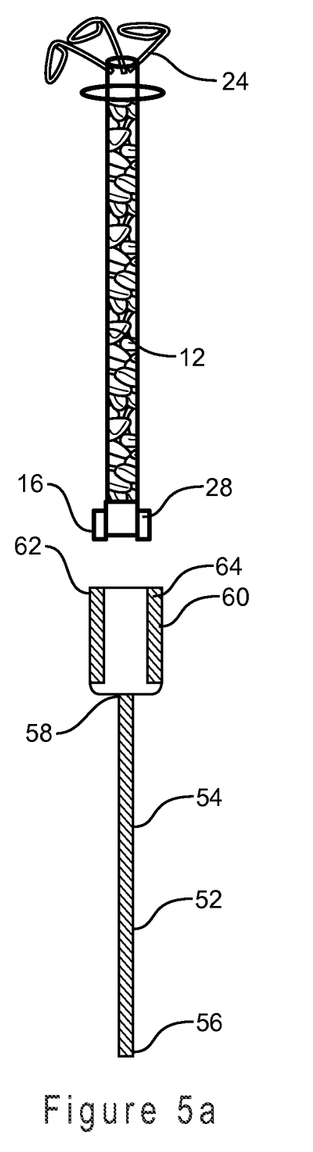
FIGS. 5a and 5b depicts an embodiment of an introduction assembly for use with the ureteral stent of FIG. 1.
Figure 5B:
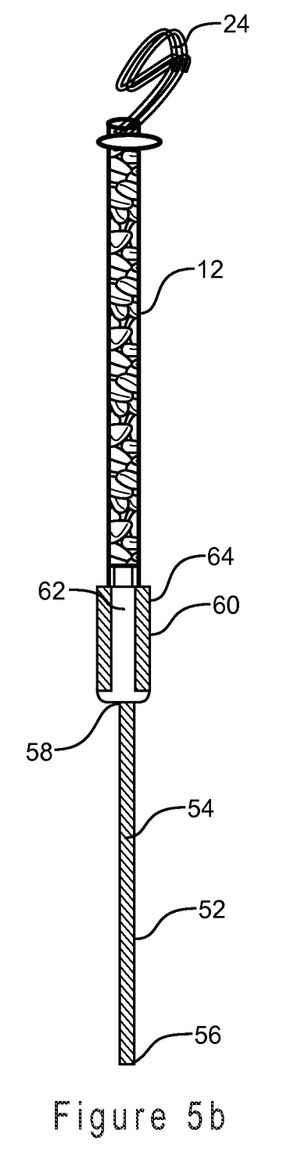

FIGS. 5a and 5b show an embodiment of the introduction assembly 52 in greater detail. As shown in FIG. 5a, the introduction assembly 52 comprises a wire shaft 54 having a proximal portion 56 and a distal portion 58. A housing 60 is disposed on the distal portion 58 of the introduction assembly 52. The housing 60 will have an opening 62 configured to receive the proximal end 16 of the ureteral stent 12. A first magnet 64 is disposed within an interior surface of the housing 60. The first magnet 64 is configured to removeably engage with the corresponding magnet 28 on the proximal end of the ureteral stent 12. The proximal portion 56 of the introduction assembly 50 is configured to remain outside of the patient. Referring now to FIG. 5b, the introduction assembly 52 helps maintain the ureteral stent 12 in an undeployed position and the tetracoil anchoring mechanism 24 in the collapsed configuration. The interaction between the first magnet 64 and the magnet 28 of the ureteral stent 12 also causes the four coil wires 25 of the tetracoil anchoring mechanism 24 to remain in the collapsed configuration. In order to deploy the ureteral stent 12, a second magnet may be attached to the proximal end of the introduction assembly 52. The second magnet would be configured to have a stronger magnetic pull force than the first magnet 64. The second magnet may be used to release the connection of the first magnet 64 and the magnet 28 disposed on the ureteral stent 12, which allows the tetracoil anchoring mechanism 24 to expand to the open configuration.

In use, this method, a physician places a wire guide through a urethra, bladder, and a ureter into a kidney. After the wire guide is placed, the access sheath 66 is guided over the wire guide. The distal opening 72 of the access sheath 66 is generally positioned at or near the ureteropelvic junction of the patient. The ureteral stent 12, held in an undeployed position by the introduction assembly 52, is inserted into the access sheath 66 and advanced through the inner lumen of the access sheath 64. A stent positioner may be used to advance the ureteral stent 12 through the access sheath 66. The ureteral stent 12 is advanced through the access sheath 66 until the distal end 18 of the ureteral stent 12 exits the distal opening 72 of the access sheath 66. Once the ureteral stent 12 is in the correct position near the utereopelvic junction, the introduction assembly 52 is rotated and the tetracoil retention assembly 24 expands into the open configuration. The position of the stent positioner is maintained by the physician while withdrawing the access sheath 66. The introduction assembly 52 may be removed by applying the second magnet to the proximal portion 56 of the wire shaft 52 and moving the second magnet in the proximal direction. This continual withdrawal of the introduction assembly 52 and the access sheath 66 allows the ureteral stent 12 to expand and deploy within the ureter. Following the deployment of the ureteral stent 12, the physician can remove the stent positioner and the access sheath 66 from the patient.

Figure 6:
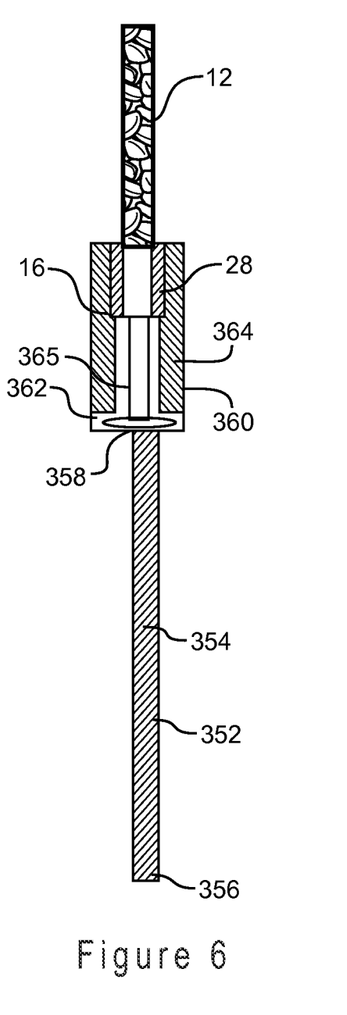
FIG. 6 depicts an alternative embodiment of an introduction assembly for use with the ureteral stent of FIG. 1.

FIG. 6 shows an alternative embodiment of the introduction assembly 352. The introduction assembly 352 comprises a wire shaft 354 having a proximal portion 356 and a distal portion 358. A housing 360 is disposed on the distal portion 358 of the introduction assembly 352. The housing 360 has an opening 362 configured to receive the proximal end 16 of the ureteral stent 12. A magnet 364 is disposed within an interior surface of the housing 360. The magnet 364 is configured to removeably engage with the corresponding magnet 28 on the proximal end of the ureteral stent 12. The interaction between the first magnet 360 and the magnet 28 of the ureteral stent 12 also causes the four coil wires 25 of the tetracoil anchoring mechanism 24 to remain in the collapsed configuration. A spring loaded piston 365 is disposed within the housing 360 proximal to the first magnet 364. The piston 365 is engaged with the proximal end 16 of the ureteral stent 12 and the distal portion 358 of the wire shaft 354. In use, a physician presses on the spring loaded piston 365 with the distal portion 358 of the wire shaft 354. This action causes the piston 365 to push against the proximal end 16 of the ureteral stent, disengaging the magnet 28 on the ureteral stent 12 from the magnet 364 of the introduction assembly, which in turn releases that tetracoil anchoring mechanism 24. The proximal portion 356 of the introduction assembly 352 is configured to remain outside of the patient.

Throughout this specification various indications have been given as to preferred and alternative embodiments of the invention. However, the foregoing detailed description is to be regarded as illustrative rather than limiting and the invention is not limited to any one of the provided embodiments. It will be evident to one skilled in the art that modifications and variations may be made without departing from the spirit and scope of the invention. Changes in form and in the proportion of parts, as well as the substitution of equivalents, are contemplated as circumstances may suggest and render expedience; although specific terms have been employed, they are intended in a generic descriptive sense only and not for the purpose of limiting the scope of the invention set forth in the following claims. Moreover, the device is not limited to any specific dimension or material discussed above, nor is the device limited to being used with saline or an image contrast fluid alone.

The invention claimed is:

1. An endoluminal prosthesis for placing in a body passage of a patient, comprising
a ureteral stent, the ureteral stent comprising a tubular housing having a proximal end and a distal end and a lumen longitudinally disposed therethrough,
a plurality of beads disposed within the lumen of the tubular housing, the beads comprising ion exchange resin material,
at least one anchoring mechanism disposed on a distal end of the tubular housing; and
a pair of porous retention screens disposed within the lumen of the ureteral stent,
wherein the pair of retention screens are configured to retain the plurality of beads and allow flow therethrough.

2. The endoluminal prosthesis of claim 1, further comprising a hydrogel film having ion exchange material disposed on the outer surface of the ureteral stent.

3. The endoluminal prosthesis of claim 1, wherein a first retention screen is disposed on the distal end of the ureteral stent and a second retention screen is disposed on the proximal end of the ureteral stent.

4. The endoluminal prosthesis of claim 1, wherein the ion exchange material comprises a sulfopropyl or sulfonate group bonded to a biocompatible polymeric material.

5. The endoluminal prosthesis of claim 1, wherein the ion exchange resin material is selected from the group consisting of chitosan-carboxymethylcellulose, a zeolite, a phenolsulfonate, an acrylate-divinyl benzene, a sulfonated polystyrene-divinylbenzene, a carboxylic acid resin, a nanoporous silica, cellulose, a phosphate or carbonic cellulose derivative, collagen, a phosphate or carbonic collagen derivative, a methyacrylate polymer, an agarose-polyacrolein, alginate, a polyvinyl alcohol sponge, and EDTA or other metal chelators.

6. The endoluminal prosthesis of claim 1, wherein the ion exchange resin material is a phosphate or carbonic cellulose derivative.

7. The endoluminal prosthesis of claim 1, wherein a magnet is disposed on a proximal end of the ureteral stent, the magnet configured to engage an introduction assembly.

8. The endoluminal prosthesis of claim 1, wherein the beads are in a packed bed configuration.

9. The endoluminal prosthesis of claim 1, wherein the beads are microporous or nanoporous.

10. A kit for placing an endoluminal prosthesis comprising,
a ureteral stent, the ureteral stent comprising
a tubular housing having a proximal end and a distal end and a lumen longitudinally disposed therethrough,
a plurality of beads disposed within the lumen of the tubular housing, the beads comprising ion exchange resin material, and
at least one anchoring mechanism disposed on a distal end of the tubular housing; and
a pair of porous retention screens disposed within the lumen of the ureteral stent;

an introduction assembly, the introduction assembly comprising
a wire shaft having a proximal end and a distal end and a first magnet connected to the distal end of the wire shaft; and
an access sheath surrounding the ureteral stent and the introduction assembly,
wherein the first magnet is configured to engage with a corresponding magnet on the at least one anchoring mechanism and wherein the pair of at porous retention screens are configured to retain the plurality of beads and allow flow therethrough.

11. The kit of claim 10, wherein the ureteral stent further comprises a hydrogel film having ion exchange material disposed on the outer surface of the ureteral stent.

12. The kit of claim 10, wherein the ion exchange material comprises a sulfopropyl or sulfonate group bonded to a biocompatible polymeric material.

13. The kit of claim 10, wherein the ion exchange resin material is selected from the group consisting of chitosan-carboxymethylcellulose, a zeolite, a phenolsulfonate, an acrylate-divinyl benzene, a sulfonated polystyrene-divinylbenzene, a carboxylic acid resin, a nanoporous silica, cellulose, a phosphate or carbonic cellulose derivative, collagen, a phosphate or carbonic collagen derivative, a methyacrylate polymer, an agarose-polyacrolein, alginate, a polyvinyl alcohol sponge, and EDTA or other metal chelators.

14. The kit of claim 10, wherein the ion exchange resin material is a phosphate or carbonic cellulose derivative.

15. The kit of claim 10, wherein the housing of the introducer assembly further includes a spring-loaded piston disposed within an interior surface.

16. A method for implanting an endoluminal prosthesis into a body, comprising,
providing a ureteral stent, the ureteral stent comprising
a tubular housing having a proximal end and a distal end and a lumen longitudinally disposed therethrough,
a plurality of beads disposed within the lumen of the tubular housing, the beads comprising ion exchange resin material,
at least one anchoring mechanism disposed on a distal end of the tubular housing; and
a pair of porous retention screens disposed within the lumen of the ureteral stent;
engaging the ureteral stent with an introduction assembly, the introduction assembly comprising a wire shaft having a proximal end and a distal end and a first magnet connected to the distal end of the wire shaft;
placing a wire guide along a body path to a location desired for the prosthesis,
inserting an access sheath along the wire guide and advancing the access sheath to the desired position;
removing the wire guide;
advancing the ureteral stent within the access sheath to the desired location using a stent positioner; and
at least partially removing the access sheath and deploying the ureteral stent by disengaging the ureteral stent from the introduction assembly,
wherein the pair of porous retention screens are configured to retain the plurality of beads and allow flow therethrough.

17. The method of claim 16, wherein the ureteral stent further comprises a hydrogel film having ion exchange material disposed on the outer surface of the ureteral stent.

18. The method of claim 16, wherein the ion exchange material comprises a sulfopropyl or sulfonate group bonded to a biocompatible polymeric material.

19. The method of claim 16, wherein the ion exchange resin material is selected from the group consisting of chitosan-carboxymethylcellulose, a zeolite, a phenolsulfonate, an acrylate-divinyl benzene, a sulfonated polystyrene-divinylbenzene, a carboxylic acid resin, a nanoporous silica, cellulose, a phosphate or carbonic cellulose derivative, collagen, a phosphate or carbonic collagen derivative, a methyacrylate polymer, an agarose-polyacrolein, alginate, a polyvinyl alcohol sponge, and EDTA or other metal chelators.

20. The method of claim 16, wherein the ion exchange resin material is a phosphate or carbonic cellulose derivative.

* * * * *